United States Patent [19]

Valinsky et al.

[11] 4,424,201
[45] Jan. 3, 1984

[54] EMPLOYMENT OF A MEREYANINE DYE FOR THE DETECTION OF MALIGNANT LEUKOCYTIC CELLS

[75] Inventors: Jay E. Valinsky; Edward Reich; Thomas G. Easton, all of New York, N.Y.

[73] Assignee: Rockefeller University, New York, N.Y.

[21] Appl. No.: 964,359

[22] Filed: Nov. 28, 1978

[51] Int. Cl.$^3$ .................. G01N 1/30; G01N 21/64; G01N 23/00; C12Q 1/04; C12Q 1/16
[52] U.S. Cl. .................................. 424/3; 424/7.1; 424/9; 435/34; 435/35; 436/64; 436/800; 436/804; 436/813
[58] Field of Search ............... 424/1, 1.5, 9, 3, 7; 435/34, 35; 436/64, 800, 804, 813

[56] References Cited

U.S. PATENT DOCUMENTS 3,673,410  6/1972  Waite et al. .................... 424/1
3,743,713  7/1973  Kato et al. .................... 424/1
3,959,455  5/1976  Ansari et al. .................. 424/1

OTHER PUBLICATIONS

Waite et al., Chem. Abstracts, vol. 76, No. 25, Jun. 19, 1972, Abstract No. 150703q.

Morse et al., Chem. Abstracts, vol. 82, No. 23, Jun. 9, 1975, Abstract No. 153152u.

Valinsky et al., Cell, 13 (1978), pp. 487-499.

*Primary Examiner*—Anna P. Fagelson
*Attorney, Agent, or Firm*—Oblon, Fisher, Spivak, McCelland & Maier

[57] ABSTRACT

A method for the detection of malignant leukocytic cells which comprises:
  contacting a fluid containing malignant leukocytic cells with a merocyanine dye of the formula:

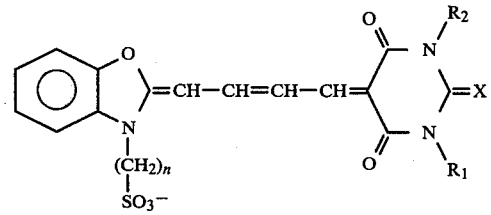

wherein n=1–5; X=O or S; $R_1$ and $R_2$ are the same or different $C_2$–$C_5$ alkyl groups:
wherein said dye is incorporated into said cells; separating the cells from the incubation mixture; and detecting said dyed cells. Fluorescence or radioactivity detection methods are preferred detecting means.

19 Claims, 4 Drawing Figures

EMPLOYMENT OF A MEREYANINE DYE FOR THE DETECTION OF MALIGNANT LEUKOCYTIC CELLS

The present invention was wholly or partially made with funds provided by the Department of Health, Education and Welfare. Accordingly, the U.S. Government has a royalty-free license under any patent granted with respect to this invention.

BACKGROUND OF THE INVENTION

1. Field of the Invention

This invention relates to a method for detection of malignant leukocytic cells.

2. Description of the Prior Art

Leukemia is a disease characterized by a marked increase in the number of leukocytes and their precursors in the blood. Other symptoms are enlargement and proliferation of the lymphoid tissue of the spleen and lymphatic glands, and marked increase in immature cells in the bone marrow. The disease is attended with progressive anemia, internal hemorrhage and increasing exhaustion. Leukemia is classified clinically on the basis of (1) duration and character of the disease—acute or chronic; (2) type of cell involved-myeloid (myelogenous), lymphoid (lymphogenous) or monocytic; (3) increase or nonincrease in the number of abnormal cells in the blood-leukemic or aleukemic.

It is widely held that changes in cell surface properties accompanying normal and neoplastic blood cell differentation are related to the molecular events underlying leukemic transformation. Differences in surface properties of normal and solid tumor cells (Inbar, M. and Sachs, L., Nature 223, 710–712 (1969)), as well as differences between normal and leukemic blood cells, have been reported (Ben-Bassat, M., Goldblum, N., Manny, N. and Sachs, L., Int. J. Cancer, 14, 367–371 (1974); Humphrey, G. B., and Lankford, J., Seminars in Oncology, 3, 243–251 (1976)). Membrane alterations associated with myelo- or lymphoproliferative diseases such as leukemia are reflected in surface adhesiveness, agglutinability with concanavalin A and lectin-induced "cap" formation (Mintz, U. and Sachs, L., Proc. Nat. Acad. Sci., USA 72, 2428–2432 (1951)). A probe that will detect leukemia-associated cell membrane changes would therefore be very useful both in the early detection of leukemia and in anticipating relapse of disease after drug-induced remission. A fluorescent or radioactive probe would be particularly useful.

Numerous extrinsic fluorescent probes have been used to study the structure and function of biological membranes (Cohen et al., J. Membr. Biol., 19, 1–36 (1974)). Members of one group of such molecules, the merocyanine dyes, have been shown to undergo transient, voltage-dependent fluorescence enhancements in response to electrical stimulation when they are incorporated into excitable membranes (Davila et al., Nature New Biol., 241, 159–160 (1973)). The generation of electrochemical potentials in human (Sims et al., Biochemistry, 13 3315–3330 (1974)) and Amphiuma red cell membranes (Hoffman and Laris, J. Physiol, 239. 519–552 (1974)), also enhance the fluorescence of some of these dyes.

However, none of these probes has been successfully used in the detection of leukemic cells. A method for the early detection of neoplastic leukemic differentiation would be useful clinically since the disease can be treated with increased success if discovered at early stages.

However, the most important problem in such a detection system, namely the ability to differentiate leukemic cells from normal cells, has not yet been satisfactorily achieved.

Ordinarily leukemia is diagnosed only by microscopic examination of smears prepared from circulating blood or bone marrow specimens that have been stained with standard dyes, such as Wright's stain; the diagnosis is basd on morphological criteria of immaturity of leukocytes and leukocyte precursors.

A need therefore continues to exist for a method which will selectively detect leukemic cells in the presence of normal cells with a high degree of accuracy and which method can be used for the early detection of leukemia as well as in monitoring the clinical course of the disease. A need also continues to exist to develop a general method for detecting the presence of solid tumors.

SUMMARY OF THE INVENTION

Accordingly, one object of the invention is to provide a method for the detection of malignant leukocytic cells, especially leukemic cells.

Another object of the invention is to provide a method for the detection of leukemic cells in the presence of normal cells. Still another object of the invention is to provide a method for the selective detection of leukemic cells by means of a fluorescent probe.

A further object of the invention is to provide a method for the selective detection of leukemic cells by means of a radioactive probe.

Still another object of the invention is to provide a method for detecting solid tumors.

These and other objects of the invention which will hereinafter become readily apparent can be attained by contacting a fluid containing malignant leukocytes with a merocyanine dye of the formula

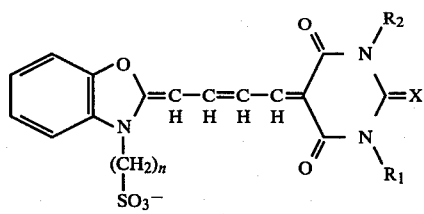

wherein n=1–5; X=O or S and $R_1$ and $R_2$ are equal or different $C_2$–$C_5$ alkyl groups; wherein said dye is incorporated into said malignant leukocytes; separating said malignant leukocytes from the incubation mixture and detecting said dyed leukocytes.

Another object of the invention has been attained by providing a method of detecting solid tumors which comprises contacting a fluid solution containing leukocytic cells derived from the blood of patients having, suspected of having or having had a solid malignant tumor with a merocyanine dye of the aforementioned formula; wherein said dye is incorporated into said cells; separating said cells from the incubation mixture and detecting said dyed cells.

In one embodiment of the invention, the detection of the malignant leukocytes is carried out by fluorescence methods. In another embodiment of the invention the dye is radioactively labelled and the detection of the malignant leukocytes is carried out by determining the radioactivity uptake of the leukocytes.

BRIEF DESCRIPTION OF THE DRAWINGS

A more complete appreciation of the invention and many of the attendant advantages thereof will be readily obtained as the same becomes better understood by reference to the following detailed description of the drawings, wherein.

DETAILED DESCRIPTION OF THE PREFERRED EMBODIMENTS

Figure 1:
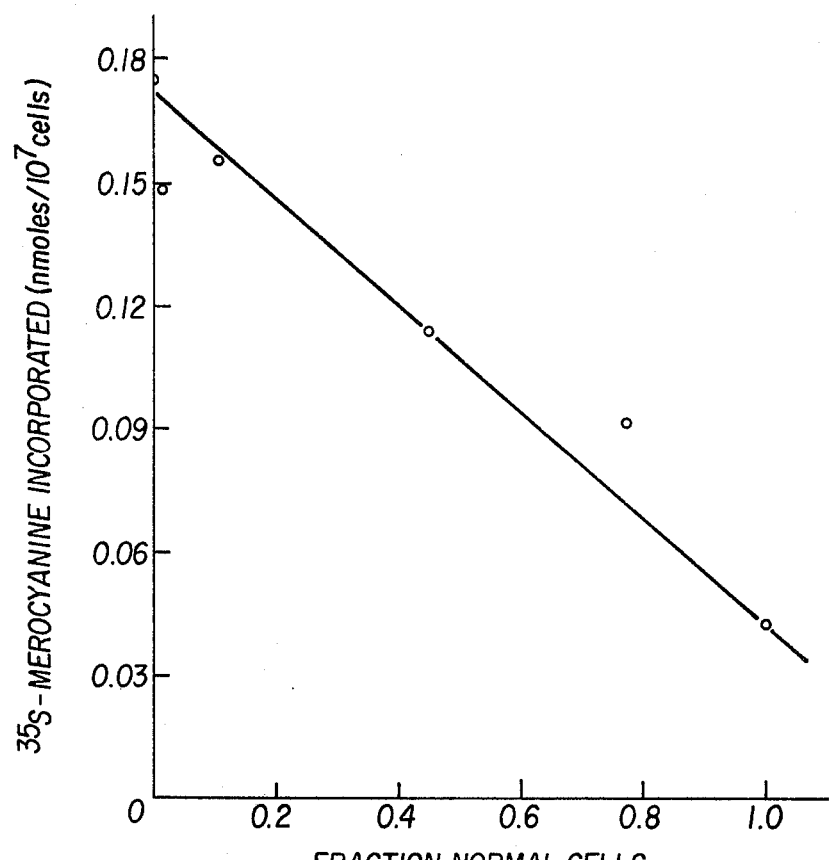
FIG. 1 describes the selective uptake of merocyanine MC540 by leukemic cells, as described in Example 79.

It has now been discovered that when a fluid containing malignant leukocytic and non-malignant leukocytic cells is mixed with a merocyanine dye of the following formula:

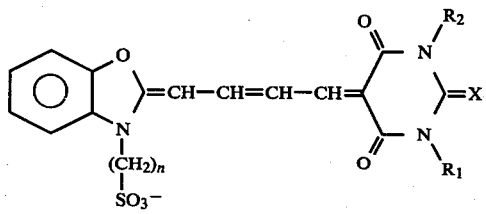

wherein $n=1-5$; $X=O$ or $S$ and $R_1$ and $R_2$ are the same of different $C_2-C_5$ alkyl groups, the malignant leukocytic cells selectively and preferentially bind the dye. Since the dye is fluorescent, the presence of malignant leukocytic cells, such as leukemic cells can be readily ascertained by measuring the fluorescence of the cells after separation from the final mixture; or when the dye is radioactive, by radioactivity uptake of the cells.

A preferred embodiment of the reaction is the use of the dye for the detection of leukemic cells.

The essence of the invention is that normal mature circulating leukocytes do not absorb any detectable quantities of dye while, regardless of the type of leukemia, more than 90% of the circulating leukocytes from individuals with the disease, take up the dye.

A wide range of leukemic cells can be readily detected by this method. Examples of detectable leukemic conditions are chronic lymphocytic leukemia, acutte lymphocytic leukemia, acute monocytic leukemia, chronic myeloctyic leukemia, acute myelocytic leukemia, chronic monocytic leukemia, acute myelocytic-monocytic leukemia, acute nonlymphoblastic leukemia, or the like. When two or more acute diseases are superimposed, one of them being a leukemia, it is sometimes not possible to detect the leukemia as easily as when it is present alone. Examples of such conditions are leukemia complicated by an autoimmune disease or leukemia superimposed on a multiple myeloma. Such conditions however are complex and rare.

The merocyanine dye wherein $n=3$; $X=S$ and $R_1=R_2=C_4H_9$, is preferred in this method. This particular dye is referred hereinafter as MC540 (merocyanine 540).

The method as applied to leukemic cells is generally carried out as follows.

A blood sample from a suspected leukemic individual is treated so as to increase its clotting time, as for example by heparinization. Red blood cells are then removed from the whole blood by standard methods. One of such methods is for example, treatment of the blood with isotonic Dextran T500 at 37° C. for a period sufficient to separate the red blood cells. The blood may also be centrifuged, in which case the red blood cells pack below an upper layer formed by leukocytes and platelets (so-called buffy coat). The buffy coat may be removed, resuspended in physiological salt solution or serum, from which the leukocytes may be isolated by standard methods.

The erythrocyte-free blood is then treated so as to isolate and purify therefrom the leukocytic components being investigated. Standard methods for the isolation of lymphocytes, monocytes or polymorphonuclear leukocytes can be used, such as those described in Bφyum, A., Scand. J. Clin. Lab. Invest., 21, Suppl. 97, 9-109 (1968). A preferred method for the isolation of lymphocytes is to centrifuge the erythrocyte-free supernatant from the Dextran treatment at about $400 \times g$ for a time sufficient to separate a semi-solid pellet of cells. A 10 minute centrifugation is usual in this case. The pellet of cells is resuspended in dextrose-supplemented saline containing about 20% autologous plasma. This suspension is then applied to a column packed with glass beads previously equilibrated with saline and the cells are allowed to adhere to the beads at 37° C. Non-adherent cells are then removed from the beads by washing with saline containing 20% autologous plasma. If desired, further purification of the nonadherent cells can be achieved by sedimentation onto a pad of Ficoll-Hypaque at $1000 \times g$ for 10 minutes. The lymphocyte-rich fraction at the interface is removed and resuspended in saline complemented with 2% autologous plasma. A fraction enriched in mononuclear cells (that is, lymphocytes and monocytes) can be prepared by sedimenting leukocyte-rich plasma onto a pad of Ficoll-Hypaque. Generically, Ficoll is a synthetic polymer of sucrose and epichlorohydrin. Hypaque® is 3,5 diacetamido-2,4,6-triiodobenzoic acid. Alternatives to Ficoll-Hypaque® are urografin-methyl-cellulose, metrizamide alone, Percoll® and the like.

This treatment is carried out for 15 minutes at $1000 \times g$. Cells recovered from the interface are resuspended in saline containing 2% autologous plasma.

A fraction containing polymorphonuclear cells can be recovered from the cell pellet obtained by sedimenting leukocyte-rich plasma, prepared as described above, onto a pad of Ficoll-Hypaque for 15 minutes at $1000 \times g$. The cells are washed twice and resuspended before use in saline containing 2% autologous plasma. Fractions thus prepared are contaminated with a variable, but small, percentage of erythrocytes.

When isolating cells from normal individuals, the methodology is of course analogous to the one described above. Normal cells can be used, for example as controls in the determination of dye uptake.

In order to allow the leukocytes to take up dye, a saline suspension of the cells is incubated with the dye. Preferably the cell concentration in such incubations is in the range $10^4$ to $5 \times 10^7$ per ml of saline. Most preferred range is $10^5$ to $5 \times 10^7$ per ml. The concentration of dye is preferably 0.1 μg/ml to 200 μg/ml, most preferably 5 μg/ml to 50 μg/ml. Times and temperatures of incubation can vary, but should be chosen so as to maximize uptake of a control sample of known leukocytic cells, for example. Normal times are 5 minutes to 2 hours, preferably 10–15 minutes to 1 hour, most preferably 10–20 minutes. Temperatures are in the range 0° C. to 40° C., preferably 4° to 37° C., most preferably 25° to 37° C.

In one of the embodiments of the invention the cells are examined for the uptake of dye by fluorescence methods. Regardless of the origin of the leukemia, fluorescence staining is always observed in leukemic cells, >90% of such cells being fluorescent in such case. There are variations in fluorescence intensity among individual leukemic cells. While fluorescence is generally strongest in the periphery, some cells show distinct perinuclear fluorescence as well. In contrast to the positive staining of leukemic leukocytes, those obtained from normal blood are uniformly nonfluorescent after comparable brief treatment with dye. Standard methods of fluorescence detection can be used, such as described generally in Slayter, E. M. (1970) Optical Methods in Biology, Wiley, N.Y. Preferably, after incubation the cells are centrifuged, washed with plasma-containing saline and then examined in a wet-amount preparation by phase-contrast and darkfield fluorescence microscopy. Stained cells can be examined at magnification suitable to distinguish individual leukocytes. A usual magnification is 1250×. Fluorescence excitation wavelength is in the range 400–700 nm, preferable 450–600 nm, most preferably 480–500 nm. In addition to standard fluorescence methods, merocyanine stained cell populations can be analyzed by flow microfluorimetry and the results presented in the form of histograms of fluorescence intensity (Horan, P. K. and Wheeless, L. L. Science 198, 149–157 (1977)).

In another embodiment of the invention, the dye is made radioactive and the cell uptake of dye is determined by standard radioactivity measurements. Any radioactive nucleus can be used, such as $^{14}C$, non-exchangeable $^3H$ or $^{35}S$. It is preferable to use $^{35}S$-dye, most preferably $^{35}S$-MC540. MC540 can be easily labeled in the 2 position of the thiobarbituric acid residue by exchange with elemental $^{35}S$ in pyridine using the method of Moravek et al, (Science 138, 146 (1962)). The radioactive dye can be purified by chromatography.

Incubation of the dye with leukocytes is carried out as above for the non-radioactive incubation. The specific activity of the dye is chosen so as to give statistically significant radioactive counts when measured against a background of normal cell uptake. Usually the specific activity of dye is 0.1 to 100 Ci/mole, preferably 1 to 50 Ci/mole, most preferably 5 to 15 Ci/mole. Higher specific radioactivity could also be used if miniaturization of assay procedures were desirable. The concentrations of cells and of dye are those described previously. After incubation, the reaction is stopped by addition of autologous plasma to 20%, the cells are collected by centrifugation, washed and assayed by radioactivity incorporation either by counting dried filtered cells, or by counting the final cell pellet dissolved in concentrated alkali, such as for example 1 M NaOH or KOH. Counting can normally be carried out by liquid scintillation in standard appropriate cocktails, such as for example liquifluor ®/toluene or Aquasol 2 ®. Both these cocktails are trademarks of New England Nuclear Corporation. Dye incorporation by leukemic cells is always substantially greater than by normal cells; the uptake ratio of leukemic to normal cells varies from 5–10 at a cell concentration of $10^7$ cells/ml for 15–30 minute periods of incubation.

After extensive experimentation it was discovered that although normal cells bind some radioactive dye most of the radioactivity bound to such normal cells is due to a combination of radioactive contaminants in the radioactive merocyanine preparation and to dye absorbed to trypsin-sensitive protein; i.e. trypsin treatment readily removes counts from normal cells. Minor radioactive contaminants of the dye are difficult to eliminate totally. However, most of the counts absorbed by leukemic cells are due to dye. 95% of the radioactivity incorporated into leukemic cells consists of intracellular dye in sites inaccessible to proteolysis of trypsin; i.e., the uptake cannot be reversed by tryptic treatment. Such leukemic cell-associated dye uptake cannot be reversed either by repeated centrifugation or washing with plasma, whose proteins have a high affinity and capacity for dye binding.

The radioactive uptake of dye by leukemic cells clearly indicates that the difference in fluorescence staining between both types of cells is in fact due to different uptakes and not to equal uptakes with artifactual different fluorescence properties. In other words, both methods are equivalent and can be used interchangeably depending on available analytical facilities. In one of the preferred embodiments of this invention, uptake of merocyanine dye by leukemic cells is carried out in the presence of illumination, since such illumination enhances the staining and radioactivity incorporation. By exposing leukemic lymphocytes to graded increments of light from an electronic flask, cellular uptake of dye is in linear relationship to the amount of illumination and is non-saturable. A small, apparently saturable increase in dye uptake by normal cells is also observed, but it is suspected that this is due to a non-identified, non-fluorescent photoproduct of the dye. Illumination can be carried out with ambient visible radiation for periods of time analogous to those used during the dark incubation. The uptake of dye is independent of ionic strength, of $Ca^{+2}$ concentration, $La^{+3}$ concentration or to the presence of the divalent metal ion chelator ethylene glycol bis(β-amino-ethyl ether)N,N'-tetraacetic acid. It proceeds equally well in isotonic saline buffers, in isoosmotic buffered sucrose or in saline with low concentrations of added serum or plasma. Kinetics of dye uptake are generally biphasic both in the light or dark and in the presence or absence of oxygen. Uptake is slightly decreased when oxygen is removed from the incubation solution, but it is never completely eliminated. Uptake, although not easily reversible by trypsin or washing with plasma, does become reversible upon washing with organic solvents, such as for example ethanol, acetone, methanol, butanol, ethyl acetate, or ionic and non-ionic detergents. This indicates that dye is not extensively metabolized nor bound covalently to cellular components.

Dye uptake is kinetically complex; it is influenced by light and oxygen, and perhaps by other and still unidentified variables. Since each of these parameters may be sensitive to cell concentration, the rate-limiting factors might vary either with cell concentration or with changing conditions during incubation. For example, both the rate and extent of oxygen depletion would be affected by cell concentration; similarly, the effective illumination of cell suspensions would be reduced by the greater turbidity associated with higher cell concentrations. It remains uncertain how the interaction of these variables under different conditions affects the uptake of dye.

Valinomycin and other similar ionophores such as nigericin, monensin, Ca ionophores X-537A and A23187 have no effect on dye uptake into leukemic cells, although valinomycin stimulates dye uptake by normal cells. This constitutes still another substantial difference in the incorporation reaction. As described above, the detection of leukemia cells is highly selective over normal mature cells. There is, however, a small and easily corrected- for interference by non-viable circulating cells. Such cells do absorb dye and it is therefore necessary to correct for their presence when staining is analyzed by fluorescence microscopy. All dead cells are freely permeable to the dye and appear brightly stained. It is therefore another embodiment of the invention to monitor the quantity of nonviable cells by the use of the dye trypan blue. This dye, as described in Conn, H. J., Biological Stains, 7th edition, Biochemical Publications, N.Y. (1961) only stains dead cells.

ity characteristics of these, and leukemic cells. However, the presence of circulating immature hemopoetic cells is very small compared to the total number of circulating adult normal cells, (less than 1%) so that this source of non-specific uptake can be readily accounted for.

The dye diagnostic test is ideally suited for monitoring the clinical course of leukemic disease such as, in drug-induced remissions, or of impending relapses. The spectral properties of the dye are favorable for its use in automated cytofluorographic applications; these might be useful for screening populations at risk for leukemia, as well as for detecting preleukemic states. In addition, the staining reaction may prove applicable to the isolation of subpopulations of hemopoietic precursor cells by fluorescence-activated cell-sorting methods.

Because some of the physiological processes that are associated with malignant neoplastic disease due to the presence of solid tumors have much in common with those occurring in leukemia, the circulating leukocytes in such solid tumor patients also are permeable to, and can be stained by the dye. While the staining intensity in Trypan Blue

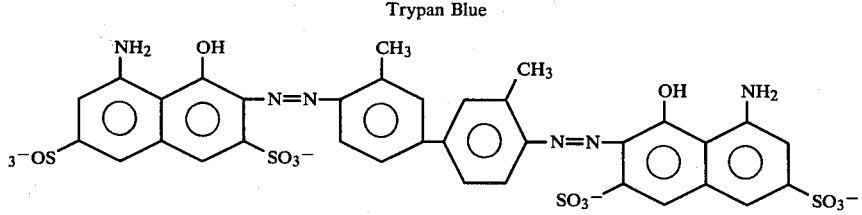

It has now been discovered that, in addition, trypan blue can also be used as a counterstain, since it quenches the merocyanine dye fluorescence associated non-specifically with dead cells. It is important to note that trypan blue in the extracellular medium does not quench the fluorescence due to merocyanine dye incorporated into viable cells. Quenching is observed only when the proximity requirements for energy transfer are met, for example, when the two dyes are adsorbed to closely adjacent intracellular sites, as occurs when a cell is freely permeable to both. Hence in practice, the fluorescence of cell suspensions incubated with merocyanine dye is assessed microscopically both before and after exposure to trypan blue to determine the proportion of stained nonviable cells. This procedure reveals that the proportion of fluorescent cells quenched by trypan blue never exceeds 20% of the stained leukemic cell population, and that the difference in merocyanine dye permeability of normal and leukemic cells can therefore not be attributed to differences in viability under the experimental conditions. In contrast, the occasional fluorescence seen in preparations of normal cells is invariably quenched by trypan blue. Use of trypan blue also indicates that vigorously illuminated, dye-treated leukemic lumphocytes lose viability after the dye absorption. No reduction in viability is observed when dye is taken up in the dark. The loss of cell viability upon vigorously illuminated dye uptake is of course of no significance to the present diagnostic methodology.

Other types of cell which also absorb the merocyanine dye are some hemopoetically immature ones, such as those obtained by gentle dissociation of normal murine thymus, lymph node, spleen or bone marrow. Dye incorporation into immature normal hemopoetic cells is probably due to similarities in the membrane permeability leukocytes from such individuals with malignant disease (e.g. carcinomas of the breast, prostate, lung, bladder, etc.) is distinctly greater than that in leukocytes from normal individuals, it is less than that of leukemic leukocytes. Dye staining of circulating leukocytes can therefore also be used to detect and to monitor the course of malignant disease due to solid tumors.

Having now fully described this invention a further understanding can be obtained by reference to certain specific examples which are provided herein for purposes of illustration only and are not intended to be limiting unless otherwise specified.

EXAMPLES 1–34

The blood of 35 leukemic individuals was tested using the diagnostic test of the present invention and compared to normal blood.

Heparinized whole blood, from leukemic or normal subjects, was treated with 1/5 vol of isotonic dextran T500 [Pharmacia; 6% in phosphate-buffered saline (pH 7)] for 1 hr. at 37° C. to remove red cells. The supernatant leukocyte-rich plasma was removed, and the cells were sedimented at 400×g for 10 min. at 4° C. The cells were then resuspended in saline (145 mM NaCl, 3 mM KCl, 1 mM CaCl$_2$, 1 mM MgCl$_2$, sodium phosphate buffer 5 mM (pH 7.0) supplemented with 10 mM dextrose) containing 20% autologous plasma, applied to a column of glass beads (20μ beads, Cataphote Division, Ferro Corporation, Jackson, Miss.) previously equilibrated with saline, and allowed to adhere to the beads at 37° C. for 30 minutes; nonadherent calls were then removed with 1-2 column volumes of saline containing 20% autologous plasma. Further purification of nonadherent cells was achieved by sedimentation onto a pad of Ficoll-Hypaque (4:1) at 1000×g for 10 minutes at 4° C. The lymphocyte-rich fraction at the interface was removed and resuspended in saline containing 2% autologous plasma.

Cells ($1\times10^5$–$5\times10^7$ cells per ml) obtained by the method described above were stained in a final volume of 1 ml of saline containing 2% autologous plasma and MC540 (40 μg/ml) for 15 minutes during illumination at a distance of 10–15 cm from a GE 15 watt "Daylight" lamp. The staining reaction was terminated by the addition of autologous plasma to a final concentration of 20%, followed by centrifugation. The cells were washed twice with saline containing 2–5% autologous plasma. Wet-mount preparations of the cells were then examined by darkfield-fluorescence and phase-contrast microscopy. The leukemic samples consisted of 28 cases of chronic lymphocytic leukemia (CLL), five of acute lymphocytic leukemia (ALL) and one of acute myelogenous leukemia (AML). A second small series (2 CML, 1 CLL) was used to evaluate staining of polymorphonuclear cells. Fluorescent staining was observed without exception in every leukemic specimen, and >90% of the cells were fluorescent in almost all cases; this was so for both the lymphocyte-enriched and the polymorphonuclear cell populations.

EXAMPLES 35–78

Leukocytes were prepared as described for experiments 1–34 except that staining was performed in solutions containing cells (at dilutions between $10^5$ and $5\times10^7$ cells per ml), $1.75\times10^{-5}$ M $^{35}$S-MC540 (spec. act. 5–15 Ci/mole) and saline in a final volume of 1 ml. The reactions were stopped by the addition of autologous plasma to give a final concentration of 20%. The cells were collected by centrifugation at 400×g for 10 minutes, washed twice by centrifugation with 2% autologous plasma in saline, and assayed for incorporated radioactivity either by filtration of the dried filters on Whatman GF/C glass fiber filters followed by liquid scintillation counting in Liquifluor/toluene (New England Nuclear) or by dissolution of the final cell pellet in 0.5 ml of 1 N NaOH followed by liquid scintillation counting in Aquasol-2 (New England Nuclear). Liquid scintillation counting was performed in a Packard Tri-Carb Liquid Scintillation Spectrometer (Model 3385). A total of 44 leukemic patients and 20 normal specimens were studied. (Table 1)

TABLE 1

Leukemic Blood Samples Examined for Merocyanine Stainability

| Type | Number in sample |
|---|---|
| Chronic lymphocytic leukemia | 25 |
| Acute lymphocytic leukemia | 3 |
| Chronic myelocytic leukemia | 3 |
| Acute monocytic leukemia | 1 |
| Acute myelocyticmonocytic leukemia | |
| Others (usually uncertain diagnosis) | 12 |
| Acute myelocytic leukemia versus lymphoma | 1 |
| Mixed modulus-histocytic lymphoma converted to leukemia | 1 |
| Multiple myeloma superimposed on acute leukemia | 1 |
| Hairy cell leukemia versus lymphoma | 1 |
| Acute monocytic leukemia versus diffuse histocytic lymphoma | 1 |
| Unclassified myeloproliferative disorder | 1 |
| Acute lymphocytic leukemia versus acute myelocytic leukemia | 2 |
| Acute lymphocytic leukemia versus stage 4 lymphoma | 1 |
| T cell lymphoma | 1 |

TABLE 1-continued

Leukemic Blood Samples Examined for Merocyanine Stainability

| Type | Number in sample |
|---|---|
| Chronic lymphocytic leukemia versus lymphoma | 1 |
| Acute nonlymphoblastic leukemia | 1 |
| Total in sample = | 44 |

EXAMPLE 79

Uptake of $^{35}$S-MC540 by mixtures of normal and leukemic lymphocytes

Normal and leukemic lymphocytes were prepared by the method described in examples 1–34. Mixtures of the two cell types were made at various ratios in a total volume of 1 ml in saline. The cell concentration was constant at $10^7$ cells per ml. MC540 (5 μg/ml; 3 Ci/mole) was added and the cells were exposed to light for 15 minutes. The reactions were stopped by the addition of normal plasma (0.2 ml); the cells were washed, dissolved in 1.0 ml of 1 N NaOH and counted in Aquasol-2.

FIG. 1 shows that there is a linear relationship between dye uptake and fraction of leukemic cells. When aliquots of such mixtures were examined by fluorescence microscopy, the proportion of stained cells corresponded to that expected from the fraction of leukemic cells present.

EXAMPLE 80

Uptake of Merocyanine by leukemic and normal lymphocytes

Figure 2:
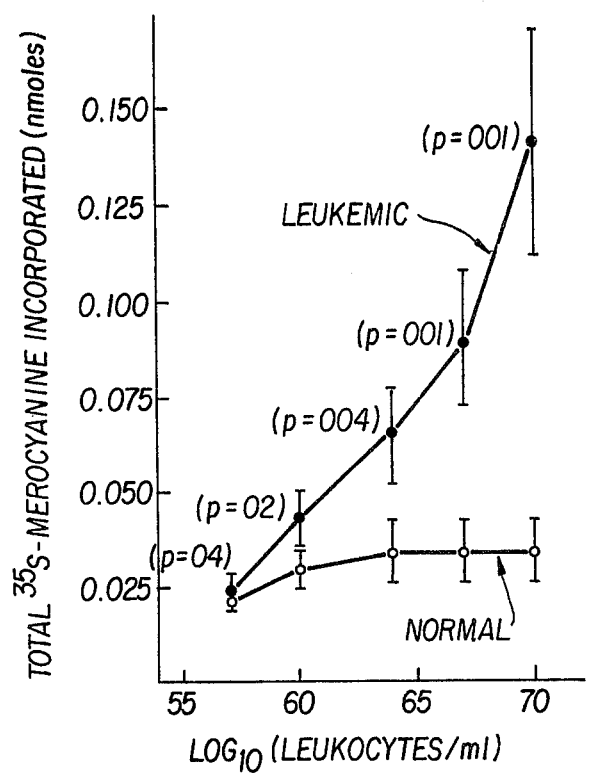
FIG. 2 describes the selective uptake of merocyanine MC540 by leukemic cells, as described in Example 80.

Leukemic and normal lymphocytes were isolated by the method of Examples 1–34 and diluted $^{35}$S-MC540 (spec. act. 5–15 Ci/mole) was added to give 10 μg/ml. The cells were exposed to light for 15 minutes. The reactions were stopped by the addition of plasma. The reaction mixtures were centrifuged and the cells were resuspended in saline. The cells were collected on Whatman GF/C filters and the filters were counted in Liquifluor, results are shown in FIG. 2. CLL cells (chronic lymphocyte leukemia) (n=20) (●—●); normal cells (n=20) (O—O). The error bars represent one standard deviation. The numbers on the leukemic cell curve represent the probability that the means of leukemic and normal cell labeling at each cell concentration indicated are the same.

EXAMPLE 81

Figure 3:
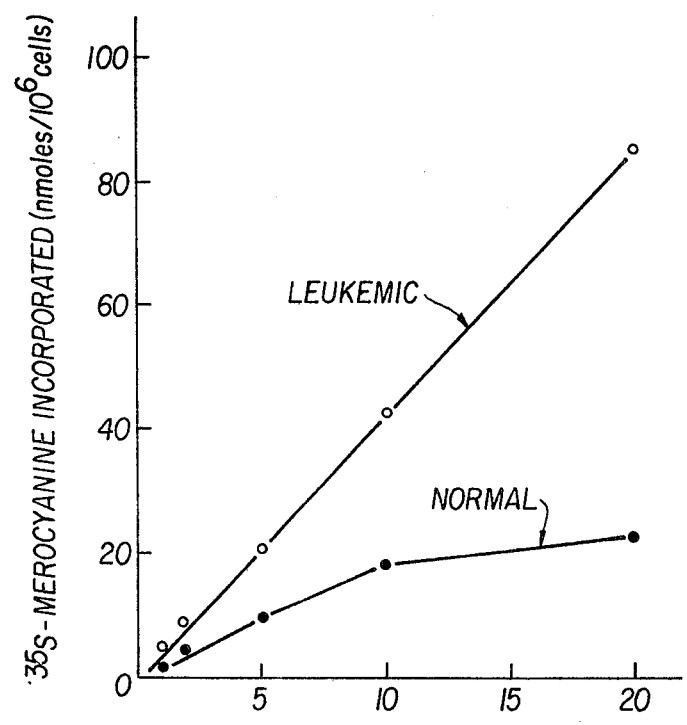
FIG. 3 shows the uptake of merocyanine MC540 by leukemic and normal cells in the presence of light, as described in Example 81.

Effect of increasing illumination on the Uptake of Merocyanine 540 by Leukemic Cells (CLL) and Normal Cells Leukemic lymphocytes were prepared by the method of Examples 1–34. The cells were diluted to $5\times10^6$ cells per ml in saline, and $^{35}$S-MC540 (spec. act. 12 Ci/mole) was added to give 10 μg/ml in a final volume of 8 ml. The cells were then exposed to light flashes. Aliquots (1 ml) were removed, the reactions were stopped by the addition of plasma, and the cells were washed, dissolved in NaOH and counted in Aquasol. Normal leukocytes were treated in an identical manner. Results are shown in FIG. 3 and indicate that leukemic lymphocytes incorporate more MC540 than normal cells in the presence of light.

EXAMPLE 82

Kinetics of uptake of MC540 in leukemic and normal cells

A fraction enriched in monuclear cells (that is, lymphocytes and monocytes) was prepared by sedimenting leukocyte-rich plasma obtained from whole blood, onto a pad of Ficoll-Hypaque for 15 minutes at $1000 \times g$. Cells recovered from the interface were washed and resuspended in saline containing 2% autologous plasma. The cells were diluted to give $5 \times 10^5$–$10^7$ cells per ml in a total volume of 8 ml of saline.

Figure 4:
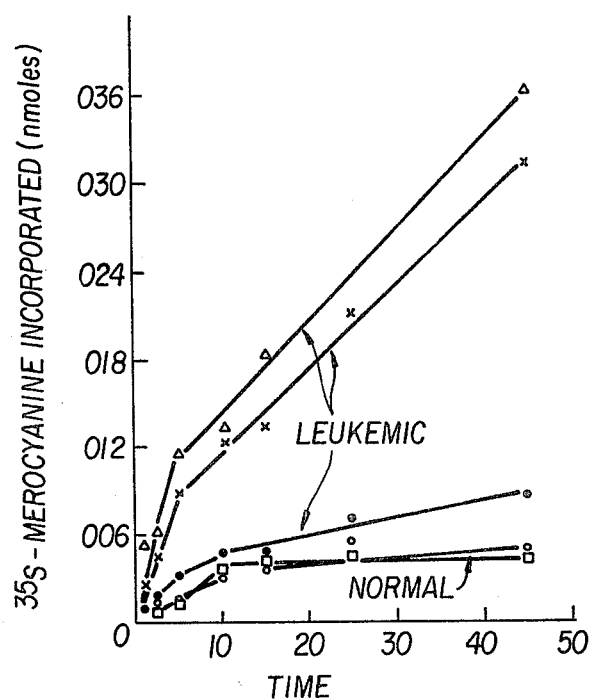
FIG. 4 shows the kinetics of uptake of merocyanine MC540 in leukemic and normal cells, as described in Example 82.

$^{35}$S-MC540 (10 μg/ml; spec. act. 14 Ci/mole) was added and the samples were exposed to low intensity light. Aliquots (1 ml) were removed at the indicated times and the reactions were quenched with 0.2 ml of autologous plasma. The cells were washed, dissolved in 1 N NaOH and counted in Aquasol, results are shown in FIG. 4. Leukemic cells: $5 \times 10^5$ cells per ml (O—O); $10^6$ cells per ml (●—●); $5 \times 10^6$ cells per ml (x—x); $10^7$ cells per ml (Δ—Δ). Normal cells: $5 \times 10^6$ per ml (□—□).

Having now fully described this invention, it will be apparent to one of ordinary skill in the art that many changes and modification can be made thereto without departing from the spirit or scope of the invention set forth herein.

What is claimed as new and intended to be covered by Letters Patent is:

1. A method for the detection of malignant leukocytic cells which comprises contacting a fluid solution containing malignant leukocytic cells with a merocyanine dye of the formula

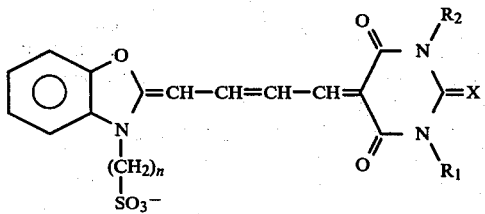

wherein $n = 1$–$5$; $X = 0$ or $S$ and $R_1$ and $R_2$ are the same or different $C_2$–$C_5$ alkyl groups;

wherein said dye is incorporated into said cells; separating the cells from the incubation mixture and then detecting said dyed cells.

2. The method of claim 1 wherein $n = 3$; $X = S$; $R_1 = R_2 = $—$C_4H_9$.

3. The method of claim 1 wherein said detection is by fluorescence.

4. The method of claim 3 wherein said detection of fluorescence is carried out by darkfield-fluorescence microscopy.

5. The method of claim 3 wherein said detection of fluorescence is carried out by flow microfluorimetric methods.

6. The method of claim 3 wherein said fluorescence is produced by excitation radiation of a wavelength in the range 400–700 nm.

7. The method of claim 1 wherein said contact is effected in a saline solution.

8. The method of claim 7 wherein said saline solution contains autologous plasma.

9. The method of claim 1 wherein the concentration of said cells in said fluid is in the range $10^5$ to $5 \times 10^7$ cells/ml.

10. The method of claim 1 wherein the concentration of said dye in said solution is in the range 0.1 to 200 μg/ml.

11. The method of claim 1 wherein the temperature of contacting is 0° to 40° C.

12. The method of claim 1 wherein said merocyanine dye is radioactive.

13. The method of claim 12 wherein said merocyanine dye is that wherein $X = ^{35}S$.

14. The method of claim 11 wherein said detection is done by determining radioactivity uptake of dye by said leukocytic cells present in said fluid solution.

15. The method of claim 11 wherein the specific activity of said radioactive dye in said solution is 0.1 to 100 Ci/mole.

16. The method of claim 1 wherein said contacting is carried out in the presence of ambient illumination.

17. The method of claim 1, wherein the incubation of said merocyanine dye with said fluid solution is carried out in the presence of trypan blue dye.

18. The method of claim 1 wherein said malignant leukocytic cells are leukemic cells which are selected from the group consisting of chronic and acute leukemias of the lymphocytic, myelocytic, myelocytic-monocytic, monocytic, nonlymphoblastic, hystocytic and lymphoma types.

19. A method of detecting solid tumors which comprises contacting a fluid solution containing leukocytic cells derived from the blood of patients having, suspected of having or having had a solid malignant tumor, with a merocyanine dye of the formula

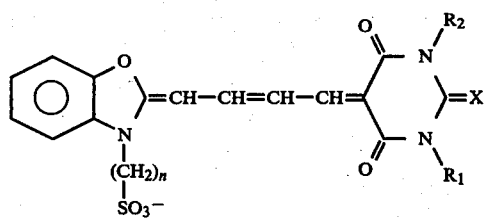

wherein $n = 1$–$5$; $X = 0$ or $S$, and $R_1$ and $R_2$ are the same or different $C_2$–$C_5$ alkyl groups;

wherein said dye is incorporated into said cells; separating the cells from the incubation mixture and detecting said dyed cells.

* * * * *